United States Patent [19]

Kochansky et al.

[11] 4,273,768

[45] Jun. 16, 1981

[54] CONTROL OF NEMATODES AND OTHER HELMINTHS

[75] Inventors: Jan P. Kochansky, Adelphi; Julius Feldmesser; William E. Robbins, both of Silver Spring, all of Md.

[73] Assignee: The United States of America as represented by the Secretary of Agriculture, Washington, D.C.

[21] Appl. No.: 151,068

[22] Filed: May 19, 1980

[51] Int. Cl.³ .......................................... A01N 57/00
[52] U.S. Cl. ................................................. 424/222
[58] Field of Search ....................................... 424/222

[56] References Cited

U.S. PATENT DOCUMENTS

| | | | |
|---|---|---|---|
| 2,436,141 | 2/1948 | Goebel | 260/461 |
| 2,683,168 | 7/1954 | Jensen et al. | 260/543 |
| 2,795,609 | 6/1957 | Jensen et al. | 260/543 |
| 3,312,623 | 4/1967 | Fitch et al. | 252/106 |
| 3,929,450 | 12/1975 | Hamm et al. | 71/86 |
| 3,988,226 | 10/1976 | Mod et al. | 204/158 HE |

FOREIGN PATENT DOCUMENTS 69357 8/1951 Netherlands.
660918 11/1951 United Kingdom.

*Primary Examiner*—Allen J. Robinson
*Attorney, Agent, or Firm*—M. Howard Silverstein; William E. Scott; David G. McConnell

[57] ABSTRACT

Some esters of alkanephosphonic acids are found to be highly lethal to nematodes and other helminths.

2 Claims, No Drawings

CONTROL OF NEMATODES AND OTHER HELMINTHS

BACKGROUND OF THE INVENTION

1. Field of the Invention

This invention relates to the control of nematodes and other helminths and more specifically to the control of these parasites with certain esters of alkanephosphonic acids.

2. Description of the Art

Phosphorous containing organic compounds are known to be useful as wetting agents and detergents, plasticizers for many plastics and resins, bonding agents for asphalt and similar compositions, lubricants, lubricant additives, corrosion inhibitors, flame proofing agents and as general agricultural household chemicals including insecticides and pesticides. They are also known to be useful as fire retardants and textile treating agents and have also been disclosed as antimicrobial agents.

A particular shortcoming in the control of nematodes is the small number of nematicides, approximately 25, that are now registered with the Environmental Protection Agency and available for use. This number, when compared to the approximately 125 herbicides and 230 insecticides registered for use, indicates the relatively primitive state of the art of nematode control. Furthermore of the 25 registered nematicides, many are restricted to specific uses and cannot be used for general treatment purposes. In addition, some are hazardous to vertebrates. Eight are organophosphates and carbamates which are hazardous not only to vertebrates but also to the surrounding environment. Nematode control capabilities are being reduced even further by severe restrictions or by cancellations, either actual or threatened, by the Environmental Protection Agency of several of the most widely used halogenated hydrocarbon fumigants.

SUMMARY OF THE INVENTION

One object of this invention is to provide a means for achieving safe, economical control of nematodes and other helminths.

Another object is to provide compounds that are lethal to nematodes and other helminths at an early larval stage of their growth cycle.

A still further object is to provide compounds that are lethal to nematodes and other helminths at concentrations far below those required with presently available materials.

In general, according to this invention certain esters of alkanephosphonic acids having chain lengths from 6 and 18 carbon atoms are found to be highly lethal to nematodes and other helminths when said parasites are exposed to the compounds at an early larval stage of their growth cycle. Compounds found to be useful for the purposes of this invention have the following general formula:

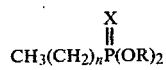

wherein n is a number from 5 to 17, X is O or S, and R is selected from the group consisting of $CH_3$, $CH_2CH_3$, $CH_2CH_2CH_3$, and $(CH_2)_3CH_3$.

DESCRIPTION OF THE INVENTION

Plant parasitic nematodes cause damage to crops in the United States estimated at about 7% of the annual total crop value. At current values, this amounts to approximately four billion dollars.

The effects of nematodes are insidious and hard to detect. Nematode damage symptoms usually develop gradually and are not specific, but rather are associated with reduced yields or with malfunctioning root systems. Nematodes are among the most difficult of all pests to control because the soil mass in which they live serves as a barrier to uniform permeation by nematicides. The soil barrier also hastens degradation of nematicidal substances thus requiring the use of large amounts to attain significant control. These factors make the use of currently available nematicides economically feasible only when the crop if highly valuable.

The difficulty in finding active compounds is partially responsible for the low number of registered nematicides. Out of thousands of compounds tested in both government and industry evaluation programs, relatively few have been found to have effective nematicidal activity. In fact, at the Nematology Laboratory, Agricultural Research Center, Beltsville, Maryland, out of 2500 chemicals screened only 36(1.4%) were lethal at concentrations of 10 ppm or less to saprophytic nematodes. Of those 36 compounds, 28 were halogenated and, upon secondary testing, all of the compounds were found to be phytotoxic and/or inactive against plant parasitic nematodes.

Consequently, it was very surprising and quite unexpected and very gratifying when we found that the alkanephosphonates of this invention displayed very high nematicidal activity.

In the preparation of the esters of the invention, the butyl esters, that is the dibutyl n-alkylphosphonates, were prepared and hydrolyzed to the phosphonic acids by the method described in J.A.C.S. 67, 1180-1182, 1945. Methyl esters were prepared by treating the acids with slight excess of ethereal diazomethane. A typical preparation of the esters is illustrated by the following preparation of dimethyl 1-tetradecanephosphonate. A solution of 160 ml dibutylphosphite and 250 ml n-heptane was prepared in a 1000 ml round bottom flask fitted with a reflux condenser, a mechanical stirrer and an addition funnel. Sodium (19 g) was added and the mixture was refluxed with vigorous stirring for 3 hours. After removal of about 1 g unreacted sodium, 162 ml tetradecyl bromide and 350 ml heptane were added and the mixture heated under reflux for 20 hours. Excess heptane (about 350 ml) was distilled off and the residue washed with successive portions (about 250 ml) of water, water+2 ml HCl, water (2×), and brine, and then dried (MgSO₄). Removal of solvent on a rotary evaporator left 248 g of an almost colorless oil. Distillation up to a temperature of 200° C./1.5 mm removed unreacted bromide and the product was collected from 220°–235° C. (almost all at 224°–228° C.) at 1.5 mm. The yield was 178.5 g of colorless liquid (55% based on sodium consumed). The dibutyl ester was pure by gas-liquid chromatography (GLC). The ester (150 g) and concentrated HCl (750 ml) were refluxed overnight, 500 ml HCL was removed by distillation and the residue allowed to cool before it was filtered. The crude solid was refluxed again with HCl as before. The second crude phosphonic acid product was recrystallized from heptane to yield 70 g of colorless platelets, mp 96°-98° C. (66% from the dibutyl ester). The acid (10 g) was treated with freshly prepared ethereal diazomethane to a permanent (>1 minute) yellow color, let stand for 10 minutes and evaporated to yield 11 g of crude ester. Two recrystallizations from pentane gave 7.9 g of pure dimethyl 1-tetradecanephosphonate, mp 32°-33° C. The product was pure by GLC and had NMR, IR, and mass spectra consistent with the expected structure.

The compounds were tested by exposing *Panagrellus redivivus,* a saprophytic nematode and a sensitive indicator of nematidical activity, to them for 48 hours in water-quartz sand-toxicant mixtures in the standard direct contact test as described in *Plant Dis. Reptr.,* 41, 527, 1957. Each compound was tested at a range of concentrations. The compounds were solubilized in a solvent-surfactant-water medium that is nontoxic to nematodes. The solvent-surfactant-water medium had the following compositions: 1 part acetone and 1 part of an aqueous solution containing 5% Tween 20 (polyoxyethylated sorbitan monolaurate) and 5% Triton X-100 (polyoxyethylated octylphenol). Approximately 400 nematodes, in all developmental stages, were exposed in each test. Effects were determined during the day immediately after exposure by microscopic examinations (Soil Science Soc. Fl. Proc. 14, 154, 1954). Normal unstressed *Panagrellus redivivus* are in continuous rapid motion, and the esophageal areas are hyaline. Exposure to nematicides results in reduced motility, immotility, and death, and when the nematodes are moribund or dead the esophageal structures disintegrate and darken. Under these test conditions, the $LD_{95}$ for a standard commercial nematicide, DD (1:1 mixture of 1,2 dichloropropane and 1,3-dichloropropene and related $C_3$ chlorinated hydrocarbons), is 36 ppm, and the lethal dosage is 40 ppm.

The concentrations of dimethylalkanephosphonates required to kill 95% exposed *Panagrellus redivivus* population in direct contact tests are shown in Table 1. Under the conditions described above the dimethyl ester of 1-dodecanephosphonic acid, compound 5 in Table 1, exhibited an $LD_{95}$ at concentrations of 0.5 to 1.0 ppm. At concentrations as low as 1.25 ppm, compound 5 has caused 100% mortality. The best commercially available nematicides, aldicarb, carbofuran, fenamiphos and phorate, require about 5 ppm in the Panagrellus assay to obtain equivalent lethal results. In addition, they are extremely toxic to mammals.

A few ethyl and butyl esters exhibited biological activity but less than that of compound 5. Some benzenephosphonates, benzenethiophosphonates, and α-toluenephosphonates also showed some activity; $C_6H_5PS(OCH_3)_2$ exhibited an $LD_{95}$ at a concentration of 40 ppm and $C_6H_5CH_2PO(OCH_2 CH_2 CH_3)_2$ exhibited an $LD_{95}$ at concentrations of about 40 to 80 ppm.

Compound 5 was further tested against second stage infective larvae of Meliodogyne incognita, a widespread economically significant root parasite which attacks a large number of cultivated crops. Larvae were directly exposed in a vial test to a range of concentrations of the test compound for 48 hours, and then washed free of the candidate toxicant. Visual examinations showed darkened, disintegrated structures in the esophageal areas of many of the exposed larvae. Viability determinations, however, were made by the following bioassay procedure. Exposed larvae were used to inoculate small nematode-free tomato seedlings (*Lycopersicon esculentum,* var. Rutgers), growing in nematode-free soil in small containers. One thousand exposed nematode larvae were placed in three or four small holes in the soil around the stem of each tomato seedling. The holes were then tamped shut and the plants were watered lightly, and thereafter maintained on a regular greenhouse schedule. Unexposed larvae were used to inoculate control plants.

*Meloidogyne incognita* causes root galls or "root-knots" in the roots at and adjacent to nematode feeding sites. These galls become macroscopically visible, due to host plant reactions involving the proliferation of abnormally large root cell masses. Infections are evaluated on an arbitrary basis, the "root-knot index", by assigning values of 0=no infection, 1.0=1-25% of the roots galled, 2.0=26-50% galled, 3.0=51-75% galled, and 4.0=100% root infection.

The inoculated tomato seedlings ere examined after three weeks to determine the viability of the nematode inocula expressed as root infections. Root-knot infections were indexed visually, and the roots were examined microscopically after differential staining to determine the absence or presence of nematodes. The results of inoculation with the exposed root-knot larvae are shown in Table II. A concentration of 20 ppm of compound 5 was sufficient to prevent any root infection, and even 10 ppm reduced infection approximately six-fold.

The mammalian toxicity of the esters of the invention appears to be quite low. None of three rabbits administered single oral dosages of 300 mg of compound 5 per kilogram of body weight died or became visibly ill. In addition, the esters would be expected to biodegrade easily and thereby not pollute the environment in which they are used.

TABLE I

| Compound | | Concentration |
|---|---|---|
| Number | Formula | ppm |
| 1 | $CH_3(CH_2)_3PO(OCH_3)_2$ | >100 |
| 2 | $CH_3(CH_2)_5PO(OCH_3)_2$ | >100 |
| 3 | $CH_3(CH_2)_9PO(OCH_3)_2$ | 20-40 |
| 4 | $CH_3(CH_2)_{10}PO(OCH_3)_2$ | 20-40 |
| 5 | $CH_3(CH_2)_{11}PO(OCH_3)_2$ | 0.5-1.0 |
| 6 | $CH_3(CH_2)_{12}PO(OCH_3)_2$ | 20-40 |
| 7 | $CH_3(CH_2)_{13}PO(OCH_3)_2$ | 80-100 |
| 8 | $CH_3(CH_2)_{15}PO(OCH_3)_2$ | >100 |

TABLE II

| | Root knot index | | | | | |
|---|---|---|---|---|---|---|
| | Concentration, ppm | | | | | Unexposed |
| replicate | 5 | 10 | 20 | 40 | 80 | control |
| 1 | 2.0 | 0.5-1.0 | 0.0 | 0.0 | 0.0 | 3.0-3.5 |
| 2 | 2.0 | <0.25 | 0.0 | 0.0 | 0.0 | 3.0-3.5 |
| 3 | 2.0 | <0.25 | 0.0 | 0.0 | 0.0 | 3.0-3.5 |

We claim:

1. A method of controlling nematodes comprising exposing said nematodes to a lethally effective amount of a compound of the formula

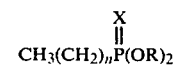

wherein n is a number from 5 to 17, X is oxygen or sulfur, and R is one of $CH_3, CH_2CH_3, CH_2CH_2CH_3,$ or $(CH_2)_3CH_3$.

2. The method of claim 1 in which the active lethal compound is $CH_3(CH_2)_{11}PO(OCH_3)_2$.